(12) United States Patent
Haas

(10) Patent No.: US 7,013,198 B2
(45) Date of Patent: Mar. 14, 2006

(54) ROBOTIC CAROUSEL WORKSTATION

(75) Inventor: Hansjoerg Haas, Burlington (CA)

(73) Assignee: Thermo CRS Ltd., Brulington (CA)

( * ) Notice: Subject to any disclaimer, the term of this patent is extended or adjusted under 35 U.S.C. 154(b) by 117 days.

(21) Appl. No.: 10/735,866

(22) Filed: Dec. 16, 2003

(65) Prior Publication Data

US 2004/0175258 A1    Sep. 9, 2004

Related U.S. Application Data

(60) Provisional application No. 60/433,598, filed on Dec. 16, 2002.

(51) Int. Cl.
*G06F 7/00* (2006.01)
(52) U.S. Cl. ............... 700/218; 700/213; 414/331.02; 414/331.05; 414/223.01; 414/226.05; 414/222.12
(58) Field of Classification Search ............... 700/213, 700/218, 245, 258, 259; 414/222.12, 223.01, 414/226.05, 331.02, 331.05, 280
See application file for complete search history.

(56) References Cited

U.S. PATENT DOCUMENTS

| 3,831,197 A | | 8/1974 | Beach et al. | |
| 4,814,592 A | * | 3/1989 | Bradt et al. ................ | 235/381 |
| 4,846,619 A | | 7/1989 | Crabtree et al. | |
| 4,864,438 A | | 9/1989 | Munro | |
| 5,143,193 A | * | 9/1992 | Geraci ........................ | 194/212 |
| 5,277,534 A | | 1/1994 | Anderson et al. | |
| 5,303,034 A | * | 4/1994 | Carmichael et al. ........ | 356/620 |
| 5,449,091 A | | 9/1995 | Dalziel | |
| 5,479,581 A | * | 12/1995 | Kleinschnitz ............... | 700/247 |
| 5,546,315 A | | 8/1996 | Kleinschnitz | |
| 5,733,024 A | | 3/1998 | Slocum et al. | |
| 5,735,587 A | | 4/1998 | Malin et al. | |
| 6,059,509 A | * | 5/2000 | Ostwald ..................... | 414/277 |
| 6,129,428 A | | 10/2000 | Helwig et al. | |

(Continued)

FOREIGN PATENT DOCUMENTS

JP   55156107 A   12/1980

(Continued)

OTHER PUBLICATIONS

Larson, David D, et al. "Storagetek 4400 Automated Cartridge System." In Digest of Papers: Eighth IEEE Symposium on Mass Storage Systems, May 11, 1987, Pp. 112-117, XP000042645, paragraph "Library Storage Module", Figures 3-5.

*Primary Examiner*—Khoi H. Tran
(74) *Attorney, Agent, or Firm*—John R.S. Orange; Santosh K. Chari; Suan X. Zhang

(57) ABSTRACT

A storage and retrieval apparatus including a robotic device capable of gripping items stored in the apparatus and delivering the item to a separate, proximate instrument. The items to be stored are loaded from the outside of the apparatus at each face of the hexagonal or octagonal shaped storage carousel. The storage carousel, which can be manually rotated, is mounted on a stationary base, both structures including a hollow core. The robotic device includes slider bars within the core of the apparatus and is rotatable about the central axis of the apparatus. The robotic device is capable of translating vertically, telescoping horizontally, rotating and gripping an item stored at a desired location within the storage carousel. Upon retrieval of a desired item, the robotic device will proceed to retract and translate downward to an aperture within the base. The item is transferred to an adjacent instrument through the aperture using the telescopic arm of the robotic device.

13 Claims, 6 Drawing Sheets

U.S. PATENT DOCUMENTS 6,357,984 B1 * 3/2002 Zinger et al. .......... 414/331.05
6,478,524 B1    11/2002 Malin
6,669,432 B1 * 12/2003 Hamel et al. .......... 414/331.05

FOREIGN PATENT DOCUMENTS

WO      WO 0216844 A    2/2002

* cited by examiner

ROBOTIC CAROUSEL WORKSTATION

This application claims benefit of Provisional Application No. 60/433,589, filed Dec. 16, 2002.

FIELD OF THE INVENTION

The present invention relates to a storage device.

BACKGROUND OF THE INVENTION

In medical, chemical and biological laboratories, microplates are commonly used as a storage medium for various types of samples used for analysis in the laboratory. A laboratory set-up is typically required to handle many samples within a given system. To increase the handling efficiency, a large number of microplates containing samples are stored together for subsequent use in a laboratory procedure. For improved efficiency in the handling of these microplates, a robotic device is typically used with the storage apparatus to remove the microplates from the store for processing and/or replace them after processing. There are several methods and apparatus currently available that are capable of storing microplates in a laboratory set-up.

Conventionally, a cylindrical carousel apparatus has been used to store small samples or cartridges for various applications as seen in U.S. Pat. No. 5,546,315 to Kleinshnitz. Such carousel storage apparatus includes a robotic device used to automate the handling and delivery of the stored samples. The device is situated in the vicinity of the rotating carousel and utilizes at least two degrees of motion to pick a sample from the carousel for delivery to another instrument within the system. One degree of motion (typically horizontal) is necessary to approach and retreat from the carousel and the other degree of motion (typically vertical) is provided to access samples above or below one another. A third degree of motion is accomplished by the rotation of the carousel.

One of the disadvantages of these existing carousel storage apparatus is that unless the destination for the placement of the sample is directly above or below the carousel, an additional degree of motion is necessary for the robotic device. This is typically rotational about an axis parallel to the central axis of the carousel, and is necessary where delivery to an instrument requires a horizontal translation. PCT publication WO 99/01894 to Zinger et al. discloses a more complex robotic device needed to acquire the third degree of motion. These required movements of the robotic device create a designated area within the system where the robotic arm can operate without interference. In a laboratory setting where it can be vital for instruments to be in close proximity, the additional space required by the delivery system is undesirable.

Furthermore another disadvantage of the existing carousel storage apparatus is that due to tie rotational movement of the carousel necessary to give the robot arm access to the array of items, it is required that a shelf structure is present to secure the items being stored and prevent these items from shifting or sliding due to the carousel's numerous movements. This can require locking mechanisms to ensure the secure placement of a sample. In addition, the rotational movement of the carousel requires that the carousel include a motor to create the rotational movement and a controller for this motor. This added complexity is in addition to the functionality required by the robotic device.

The samples stored within a cylindrical carousel tend to be spaced evenly about the circumference of the apparatus at each layer provided by the structure. Because of the finite size of the samples, the samples are distributed about the circumference and this creates an area within the core of the apparatus that becomes unused space. In a laboratory setting where space can become a vital asset, the unused space within the core increases the footprint of the storage device and utilizes additional space.

An attempt to use the unoccupied central core of a cylindrical storage apparatus as seen in U.S. Pat. No. 5,733,024 to Slocum et al., requires that the storage apparatus be of a half-cylinder rather than a complete cylinder. The storage apparatus allows a robotic device to be placed within the core of the half-cylinder, however part of the main structure must be removed to permit the delivery of the sample from the storage apparatus to another part of the system.

This arrangement not only limits the storage capacity but also delivery by the robotic device is limited to a single aperture and thus a single site in which it can deliver the desired sample to another instrument in the system.

It is thus an object of this invention to obviate or mitigate at least one of the above mentioned disadvantages.

SUMMARY OF THE INVENTION

In one aspect a storage and retrieval apparatus comprises a carousel having a plurality of articles disposed about an axis and a robotic device located within the core of the carousel. The robotic device is moveable along the axis and about the axis to align with a selected location and is moveable radially to move the item into and out of the carousel. A control system controls the axial, radial and rotational movements of the robotic device. The arm of the robotic device retrieves a sample stored about the perimeter of the carousel moves the sample to one end of the carousel and delivers the sample to another instrument.

Preferably, the carousel is located on a base having at least one aperture to permit radial movement of an item carried by the device through the base.

BRIEF DESCRIPTION OF THE DRAWINGS

These and other features of the preferred embodiments of the invention will become more apparent in the following detailed description in which reference is made to the appended drawings wherein.

Figure 1:
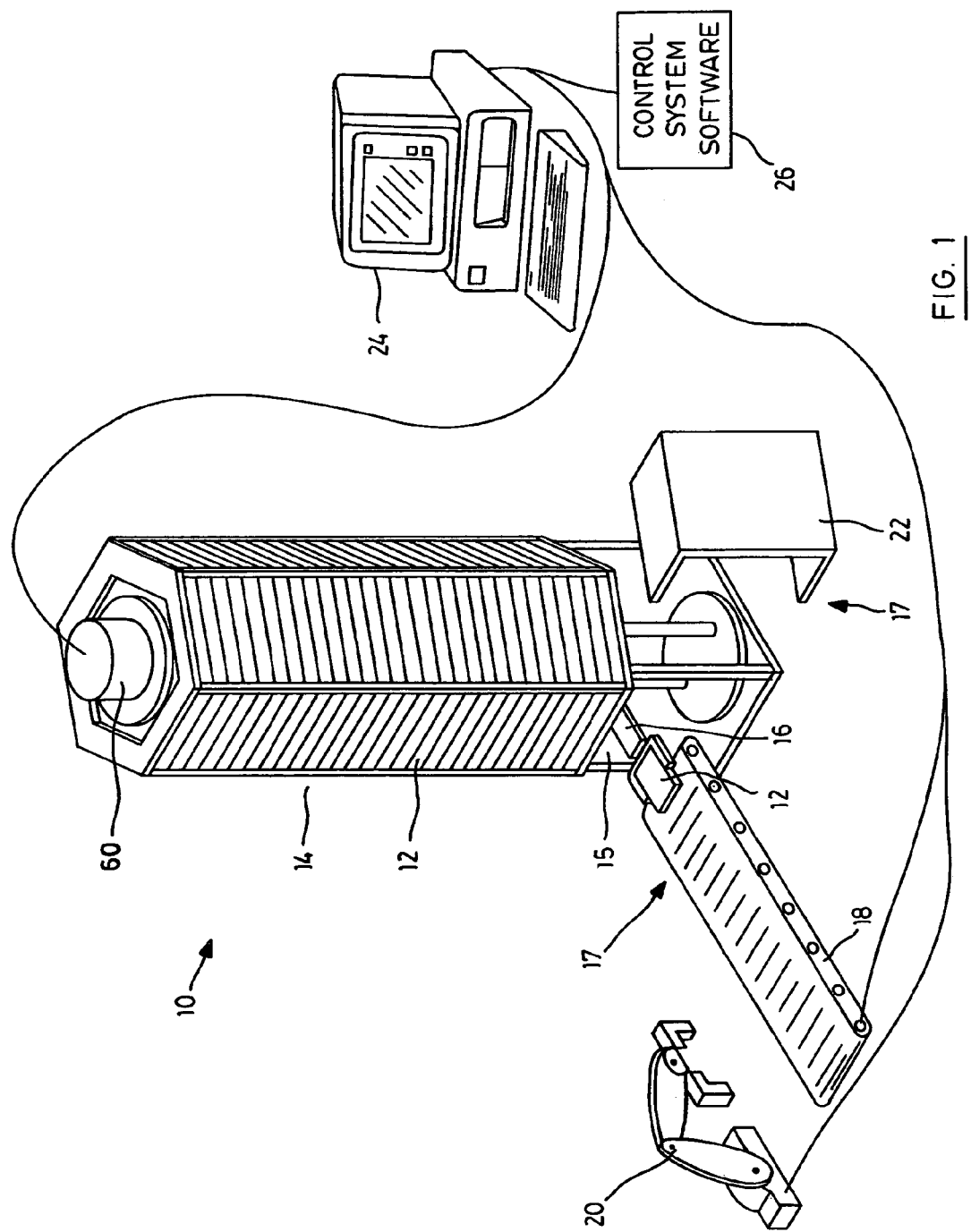
FIG. 1 is a schematic representation of an automated laboratory installation.

Referring therefore to FIG. 1, an automated laboratory installation 10 is organized to conduct repetitive test upon samples contained in containers 12 stored in predetermined locations in a carousel 14. The containers 12 are typically microplates that may have one of a number of known configurations. The carousel 14 utilizes a robotic device 16 to deliver individual containers 12 to a delivery station 15 from where they are dispensed to one of a number of workstations 17. At one of the workstations 17, a conveyor 18 transports the containers 12 to a transfer device 20. At an alternate workstation 17, the container 12 is delivered to an analyzer 22. The interaction of the components forming the installation 10 are controlled through a centralized computer system 24 implementing control system software 26. The computerized system 24 receives inputs from sensors incorporated into the components and provides control signals to motors utilized by the various components to effect the requisite sequence of events upon the containers 12. It will be appreciated that the installation 10 may utilize different components and different sequences of events and is provided by way of illustration only.

Figure 2:
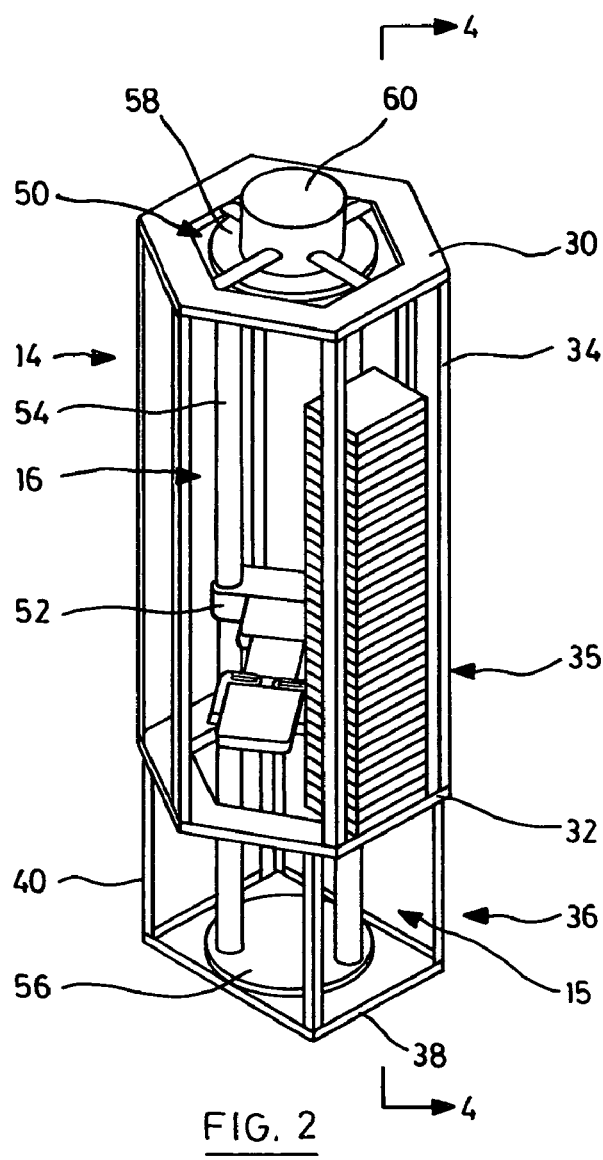
FIG. 2 is a perspective view of a carousel used in the installation of FIG. 1.

As may be seen more clearly in FIG. 2, the carousel 14 comprises a pair of end frames 30, 32 interconnected by columns 34. The frame members 30, 32 are hexagonal with the columns 34 arranged at the apices of the members 30, 32 to provide an open hexagonal frame generally indicated at 35. The frame member 32 is supported upon a plinth 36 that similarly is formed as an open frame from a base 38 and support 40.

The plinth 36 is square in cross-section and is inset from the periphery of the hexagonal frame 35 to provide an overhang. The hexagonal frame 35 may be fixed to the plinth 36 or may be rotatably supported on the plinth to allow it to be rotated manually to a preferred position.

Figure 3:
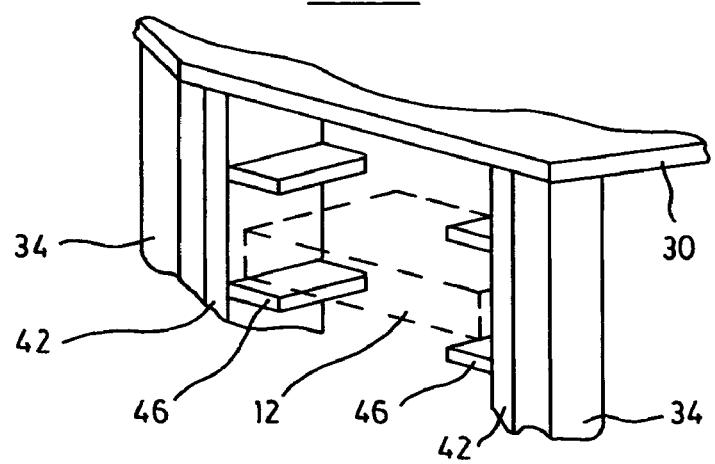
FIG. 3 is an enlarged view of a portion of the carousel shown in FIG. 2.
Figure 4:
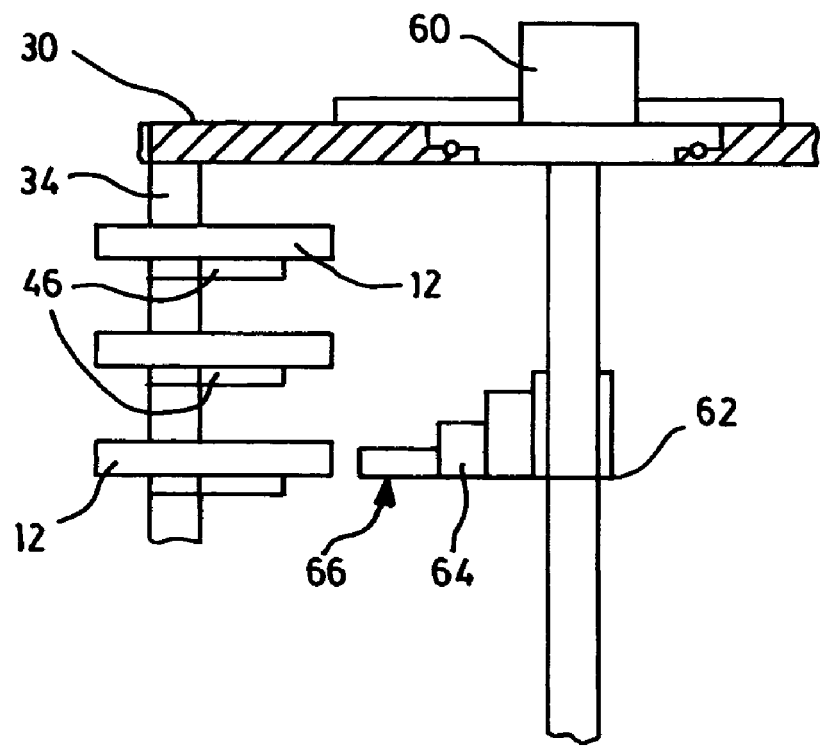
FIG. 4 is a view on the line 4—4 of FIG. 2.
Figure 4:
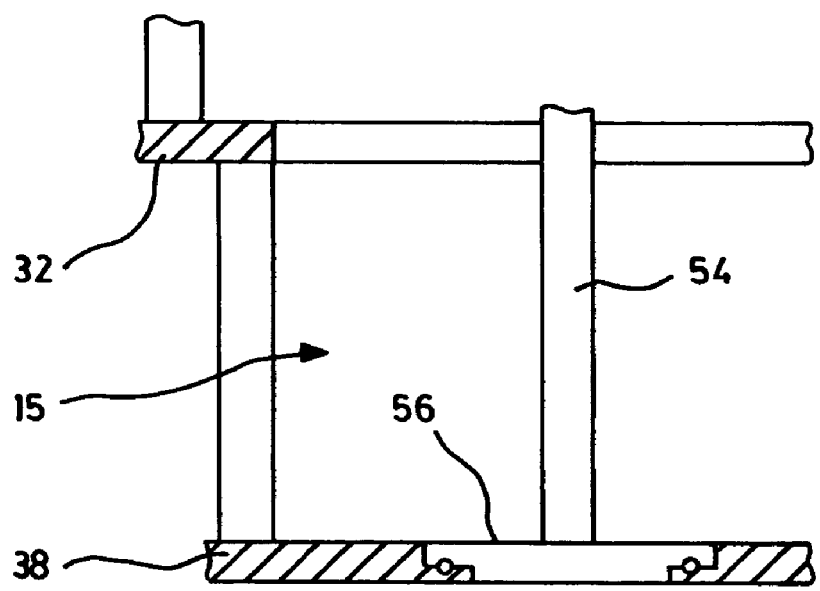

The framework 35 provides six facets that are utilized as storage racks for the microplates 12. As can be seen from FIGS. 3 and 4, the columns 34 are used to support racks 42 designed to receive and support the microplates 12 in a stacked array at each of the predetermined locations. The form of the racks 42 will depend on the configuration of the microplate but generally provide a stable and secure support for the individual microplates. In the embodiment illustrated in FIGS. 3 and 4, the rack 42 includes individual supports 46 that maintain the plates 12 in spaced horizontal relationship as a vertical array. Alternatively, the racks 42 may simply support the plates 12 that are self stacking, one on top of the other. The particular configuration chosen will depend to a certain extent upon the procedures to be performed by the installation and whether random access to each microplate is required, or whether sequential access to a stack of microplates is satisfactory.

The open framework 35 provides a central core 50 that extends through the plinth 36. Robotic device 16 is located within the core 50 and is operable to access the individual micropates 12 from the racks 42 and deliver them via the delivery station 15 to selected ones of the workstations 17 disposed about the plinth 36. As shown in the embodiments of FIGS. 2 through 5, the robotic device 16 includes a head 52 supported on a pair of bars 54. The head 52 is slidable along the bars 54 by a suitable drive mechanism, such as a driven lead screw, and the bars 54 are supported at opposite ends in a pair of turntables 56, 58. The turntable 56 is rotatably supportly in the base 38 and the turntable 58 rotatably supported on the end frame 30. A motor 60 acts between the frame 30 and the turntable 58 to rotate the turntable and therefore the robotic device 16, about the vertical axis of the carousel 14.

Figure 6:
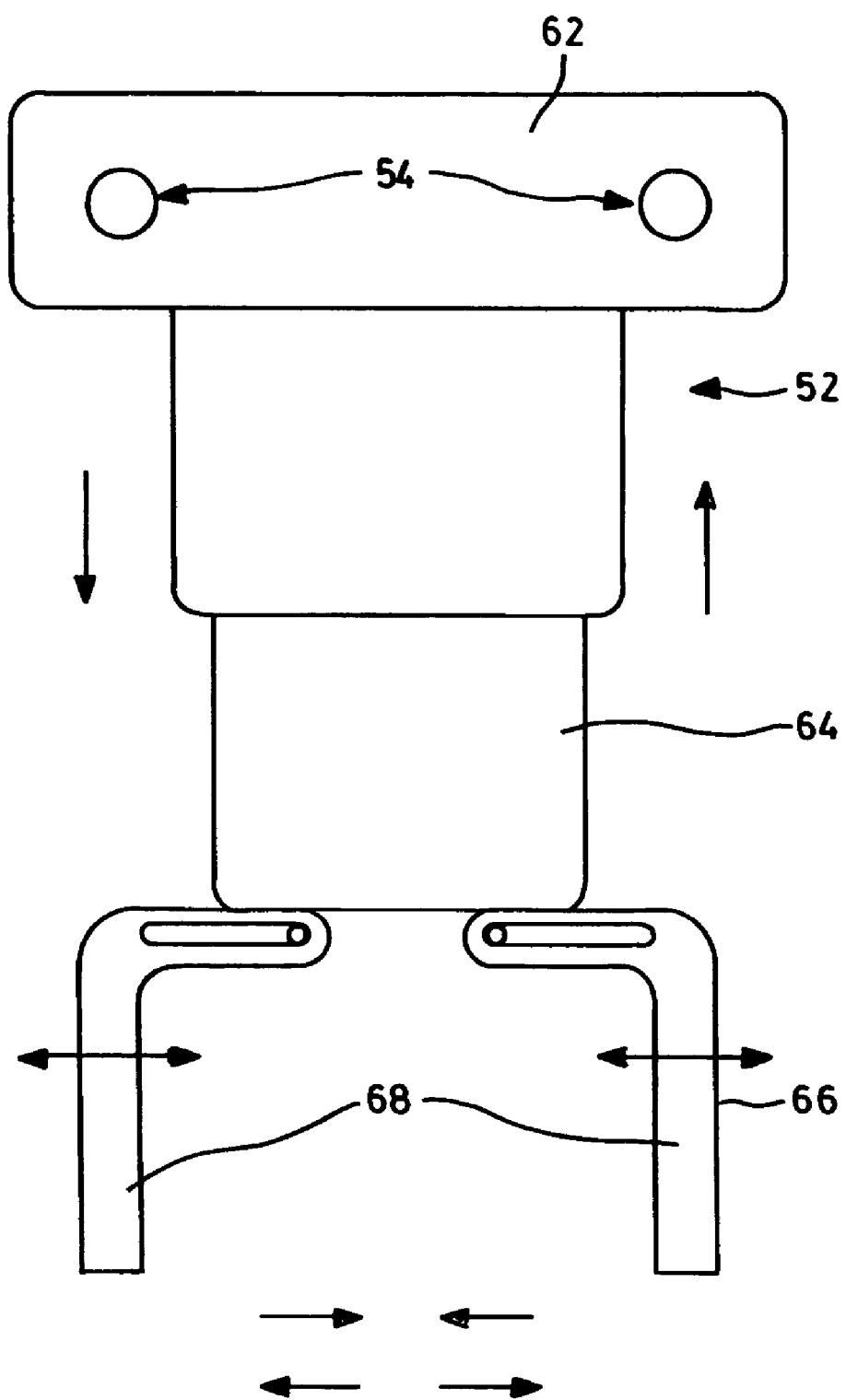
FIG. 6 is a plan view of a robotic device used with the carousel of FIG. 2.

The head 52 is shown in greater detail in FIG. 6 and includes a body 62 slidably mounted on the bars 54, The body 62 supports an arm 64 that is displaceable relative to the body 62 along a horizontal axis. As shown schematically in FIG. 6, the arm 64 telescopes within the body 62 but it will be appreciated at other mechanisms for relative movement between the body 62 and a distal end of arm 64 maybe utilized. A hand 66 is provided on the distal end of the arm 64 and has a pair of fingers 68 configured to grip the lateral edges of the microplate 12. The fingers 68 are moveable laterally relative to the arm 64 to bring them into engagement with the lateral edges of the plate 12. Movement of the body 62 along the bars 54 is controlled by a suitable actuator and may conveniently incorporated into a lead screw formed on one of the bars 54. Rotation of the lead screw will induce a vertical movement of the body 62 and carry the arm 64 and therefore the hand 68 with it. Movement of the body 62, arm 64 and fingers 68 is of course controlled by the computer 24 to provide the required sequence of events.

In operation, the carousel 14 is initially loaded with microplates 12. The device 16 is then utilized to retrieve selected microplates and deliver them to the analyzer 22 or conveyor 18 depending upon the process to be performed. To achieve this, the head 52 is positioned vertically in alignment with the required microplate 12 and rotated by the motor 60 to be orientated towards the selected microplate. The arm 64 is then extended and the fingers 68 actuated to grip the selected microplate 12. The arm 64 is then retracted to remove the microplate 12 from the stack 42 and locate it within the core 50. The head 52 is then lowered so as to be located within the plinth 36 at the delivery station 15 and oriented through operation of the motor 60 to position the microplate 12 for delivery to either the conveyor 18 or the analyzer 22. When correctly positioned, the arm 64 is extended and the microplate delivered radially to the selected one of workstations 17. The arm 64 may then be retracted and moved vertically to retrieve a further microplate or may be rotated to another workstation to engage a microplate and return it to the rack 42.

Where the microplates 12 are maintained on individual shelves 46, the head 52 may be aligned to selectively retrieve individual microplates under the direction of the computer 24. Where the microplates 12 are simply stacked one above the other in the racks 42, the arm may be positioned to retrieve the uppermost one of the stack and return the plate to the topmost layer of an alternate stack. In each case however, the device 16 is utilized to retrieve a microplate from a storage location to the interior of the carousel 14 and delivered to a delivery station located at one end of the carousel 14. In this manner, each of the facets of the hexagonal frame 35 may be utilized for storage and the workstations 17 are disposed in convenient locations about the carousel 14.

Figure 5:
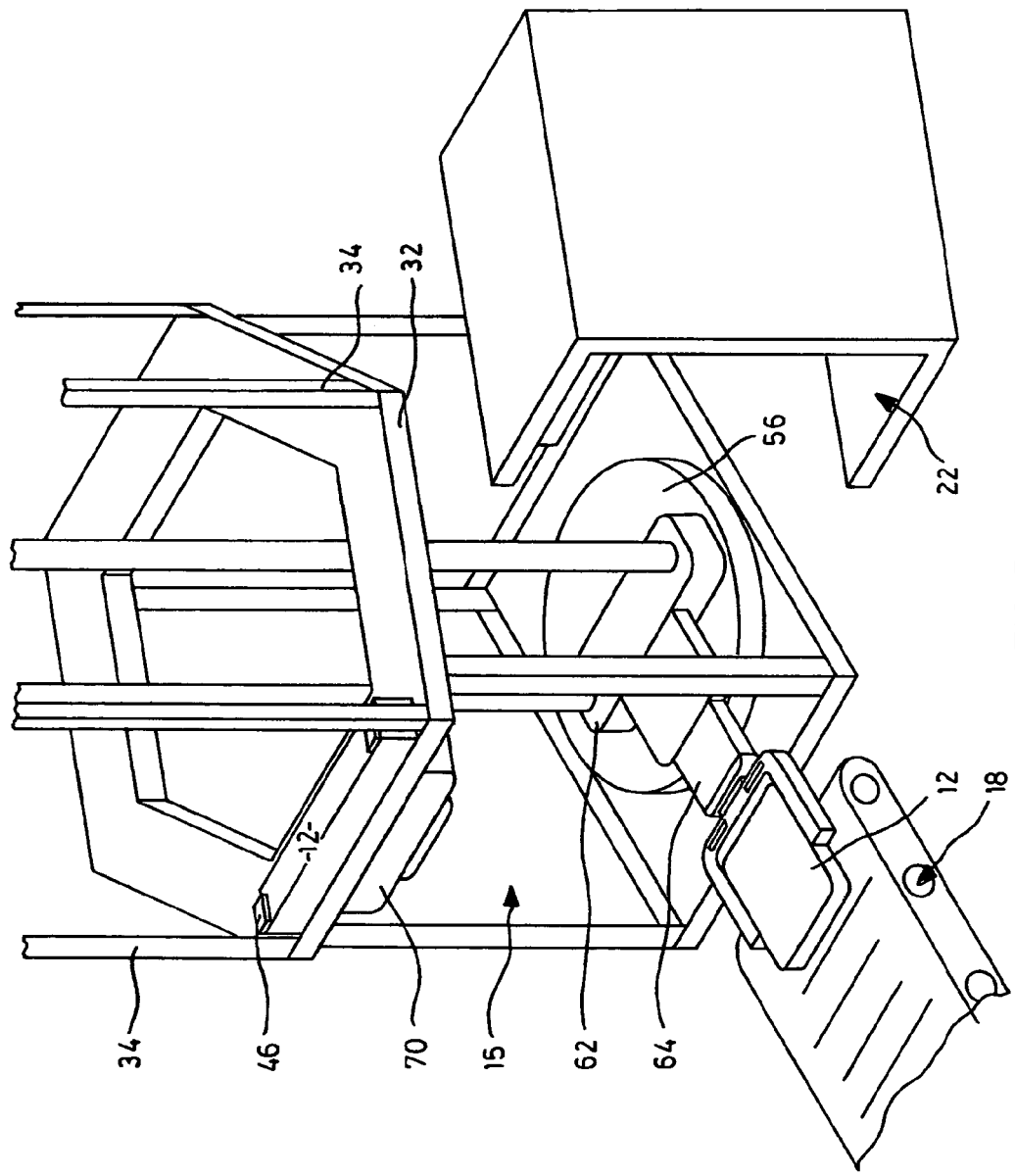
FIG. 5 is a view on an enlarged scale of the base of the carousel shown in FIG. 2.

The arrangement of plinth and carousel also facilitates the incorporation of additional functionality. As indicated in FIG. 5, a delidder 70 is supported on the underside of the lower member 32. The delidder 70 is operable to remove a lid from a microplate 12 prior to delivery to a workstation, such as the conveyor 18. Thus, as the head 52 enters the plinth 36, the arm 64 is extended to position the microplate 12 beneath the delidder 70. The delidder then functions to remove the lid and the arm continues the delivery of the delidded microplate to the conveyor 18.

Figure 7:
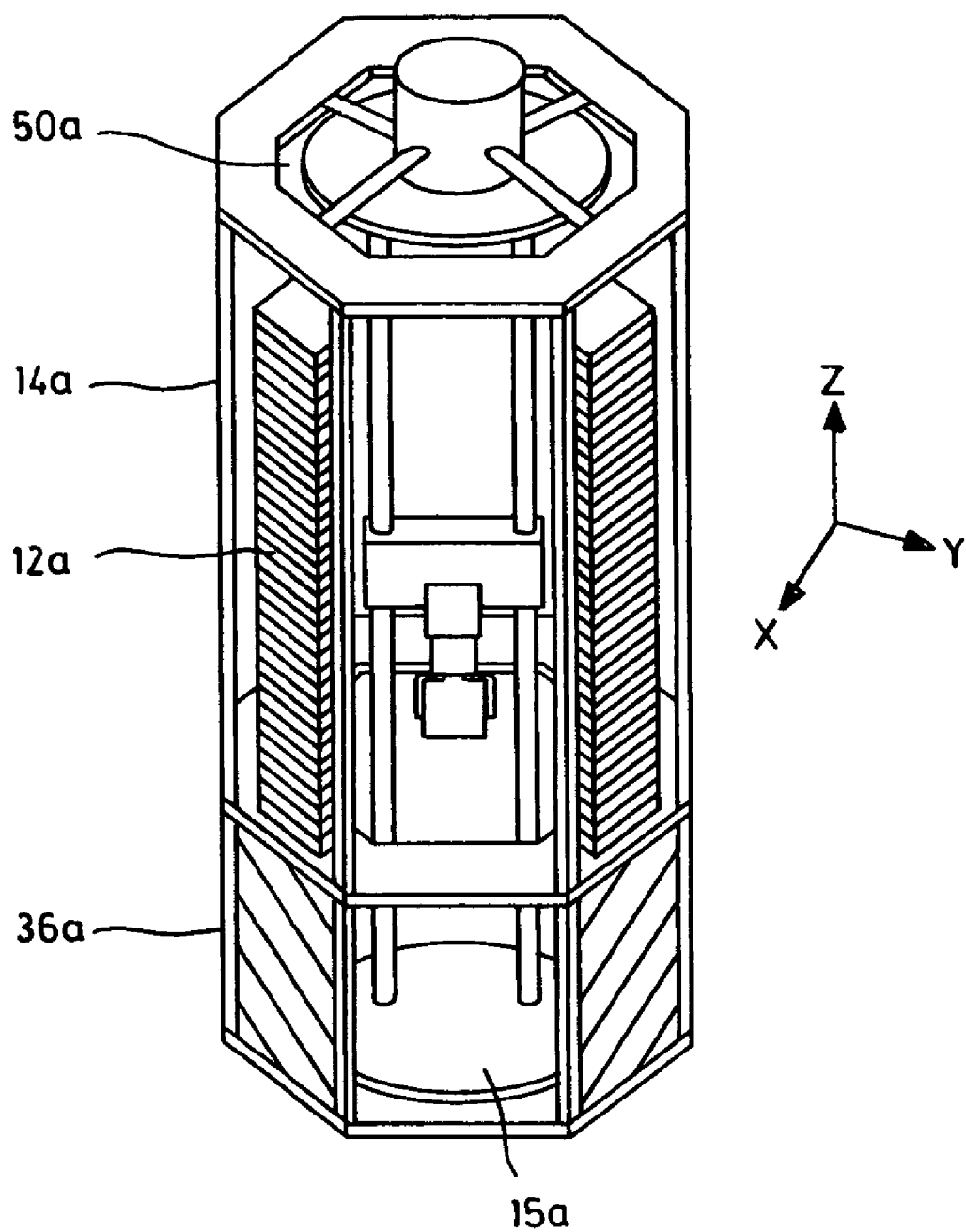
FIG. 7 is a view similar to FIG. 2 of an alternative embodiment of carousel.

In the embodiment described above, the frame 35 is hexagonal. However, other configurations may be utilized such as an octagonal figuration as shown in FIG. 7. In the embodiment of FIG. 7, in which like components will be identified with like reference numerals, with a suffix a added for clarity, the carousel 14a has eight racks 42a to support microplates 12a. A robotic device 16a is incorporated within the core 50a and is again operable to retrieve microplates from the individual arrays and deliver them within the plinth 36a. In this embodiment, the plinth 36a conforms to the shape of the carousel 14a but again permits integration of auxiliary equipment such as the delidder described above into the plinth area. The embodiment shown in FIG. 7 not only provides additional storage capability but enhances the stability of the carousel by extending the plinth to the periphery of the carousel.

It can be seen that a compact, flexible and efficient storage carousel is provided that can be easily integrated into a general system requiring the storage of a perality of samples. The samples may be loaded manually from the outer side of the carousel and a robotic device within the carousel rotates and translates to position itself adjacent to the desired sample. It is then operable to extend radially and grip the sample. The arm of the device may then move inwardly to locate the sample within the core and translate vertically to deliver the sample to the delivery station at one end of the carousel. The workstations may be located at that end of the carousel to facilitate delivery of the sample from within the core to the workstation. This permits the workstations to be located in close proximity to the carousel and reduces the overall footprint of the installation. It will of course be appreciated that the movement of the robotic device is controlled by the software program and suitable sensors and feedback signals are provided to that program as is well known in the art.

Although the embodiments described above show the delivery station 15 provided in the base at the lower end of carousel 14, it will be appreciated that a delivery station may be provided at the opposite end, ie. the upper end or intermediate the ends to meet the requirements of the workstations 17. In this latter case, the racks 42 are interrupted to provide access through the frame 35 from the core 50 to the exterior. Similarly, it is preferred that the robotic device is rotatable about the axis but rotation of the carousel on the plinth may be considered an alternative in certain situations, particularly where only a single workstation is to be serviced.

What is claimed is:

1. A storage device comprising a carousel having a plurality of locations disposed about an axis to receive articles, a delivery station axially spaced from said locations and a robotic device located within said carousel to transfer articles between one of said locations and said delivery station, said robotic device being moveable radially relative to said axis toward and away said locations and axially to between said delivery station and said location to facilitate transfer of articles within said carousel.

2. A storage device according to claim 1 wherein said robotic device is rotatable about said axis to permit alignment with different ones of said locations.

3. A storage device according to claim 2 wherein said delivery station is located at one end of said carousel.

4. A storage device according to claim 3 wherein said delivery station is located at a lower end of said carousel.

5. A storage device according to claim 4 wherein said carousel is located on a plinth and said delivery station is located within said plinth.

6. A storage device according to claim 5 wherein said robotic device is operable in said delivery station to move an article radially between said delivery station and a workstation disposed about said plinth.

7. A storage device according to claim 5 wherein said plinth is inset from said carousel.

8. A storage device according to claim 1 wherein said robotic device includes an arm supported on a body and extendible toward and away from said locations.

9. A storage device according to claim 8 wherein said body is displaceable within said carousel along said axis.

10. A storage device according to claim 9 wherein said body is rotatable within said carousel.

11. A method of moving articles by a robotic device between a delivery station and storage locations in a carousel, said method comprising the steps of moving said article radially between said location and an interior of said carousel and axially within said carousel to said delivery station.

12. A method according to claim 11 including the step of rotating said article within said carousel to orient said article relative to said carousel.

13. A method according to claim 12 including the step of moving said article radially at said delivery station toward a workstation.

* * * * *